(12) United States Patent
Collins et al.

(10) Patent No.: US 6,665,909 B2
(45) Date of Patent: Dec. 23, 2003

(54) LOW-PROFILE MOUNTING CLIP FOR PERSONAL DEVICE

(75) Inventors: Sean Collins, Canyon Country, CA (US); Sheldon B. Moberg, Granada Hills, CA (US); Dave S. Kimball, Irvine, CA (US); Timothy Payne, Santa Ana, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 10/021,885

(22) Filed: Dec. 14, 2001

(65) Prior Publication Data

US 2003/0110595 A1 Jun. 19, 2003

(51) Int. Cl.⁷ .............................. A45F 5/02; A45F 5/00
(52) U.S. Cl. ........................................ 24/3.12; 24/3.1
(58) Field of Search ...................... 24/3.1, 3.11, 3.12, 24/573.11, 580.11; 224/162, 183, 195, 197, 269, 271, 272, 652, 666, 669, 678, 930; 455/90, 100, 351, 575.1–595.9; 248/226.11

(56) References Cited

U.S. PATENT DOCUMENTS

| | | | | |
|---|---|---|---|---|
| 4,486,918 A | * | 12/1984 | Peebles ........................ 16/422 |
| 5,054,170 A | * | 10/1991 | Otrusina .................. 24/580.11 |
| 5,201,858 A | * | 4/1993 | Otrusina ................. 24/573.11 |
| 5,368,427 A | * | 11/1994 | Pfaffinger .................... 411/553 |
| 5,472,317 A | | 12/1995 | Field et al. |
| 5,666,700 A | * | 9/1997 | Anscher .................. 24/163 R |
| 5,906,031 A | * | 5/1999 | Jensen ......................... 24/3.12 |
| 6,032,339 A | * | 3/2000 | D'Addario .................... 24/649 |
| 6,108,944 A | * | 8/2000 | Savoie ......................... 36/134 |
| 6,166,695 A | * | 12/2000 | Witczak et al. ............. 343/702 |
| 6,305,588 B1 | * | 10/2001 | Michel et al. ............... 224/271 |
| 6,470,535 B1 | * | 10/2002 | Mayne et al. ................ 24/3.12 |
| 2002/0002059 A1 | * | 1/2002 | Johnson |

FOREIGN PATENT DOCUMENTS

| | | | |
|---|---|---|---|
| EP | 0 777 371 A1 | * | 6/1997 |
| JP | 10179233 A | * | 7/1998 |
| JP | 2002136322 A | * | 5/2002 |

* cited by examiner

Primary Examiner—William L. Miller
Assistant Examiner—Ruth C. Rodriguez
(74) Attorney, Agent, or Firm—Foley & Lardner

(57) ABSTRACT

A low-profile, durable mounting clip is provided for holding personal devices (such as personal electronic devices). The mounting clip may have an essentially inverted "L" shaped configuration including a foot portion having engagement elements for attachment to corresponding engagement elements on a housing of a personal device. A leg portion provides for attachment to an undergarment or other suitable article of clothing. A heel portion located between and connecting the leg portion and foot portion allows the foot portion to flexibly and durably retract from the housing for attachment. The mounting clip may include a snap tab beam locking mechanism having a barb for interlocking with a bump provided on the housing or a rotatable cam locking mechanism having one or more radial snap tabs having engagement elements for engaging corresponding surfaces on the mounting clip. Rotation of the rotatable cam locks and unlocks the mounting clip onto the housing.

24 Claims, 8 Drawing Sheets

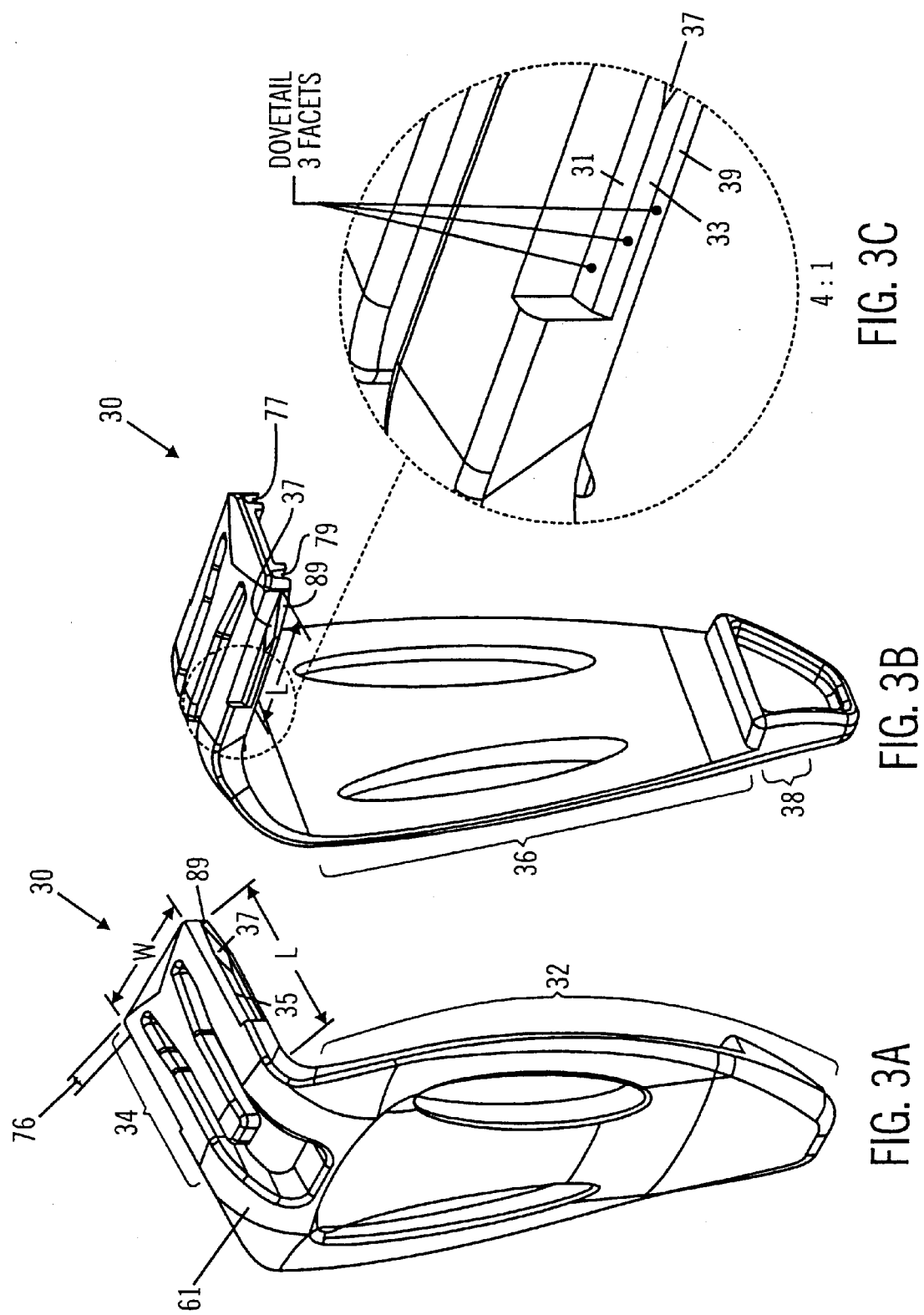

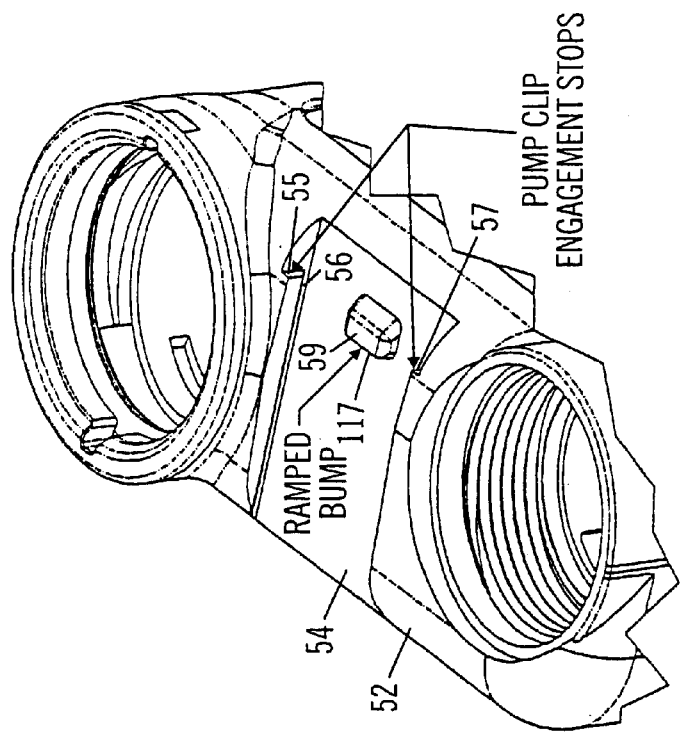
FIG. 5D
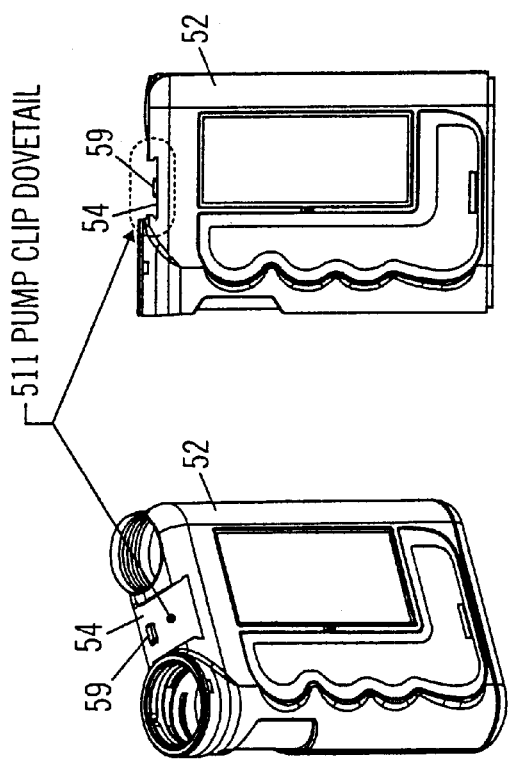
FIG. 5A
FIG. 5B
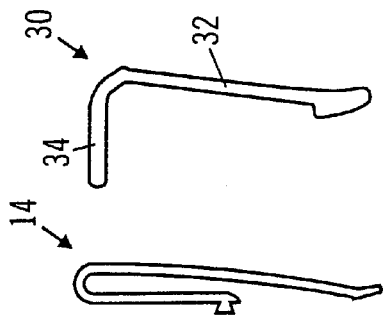
FIG. 5C

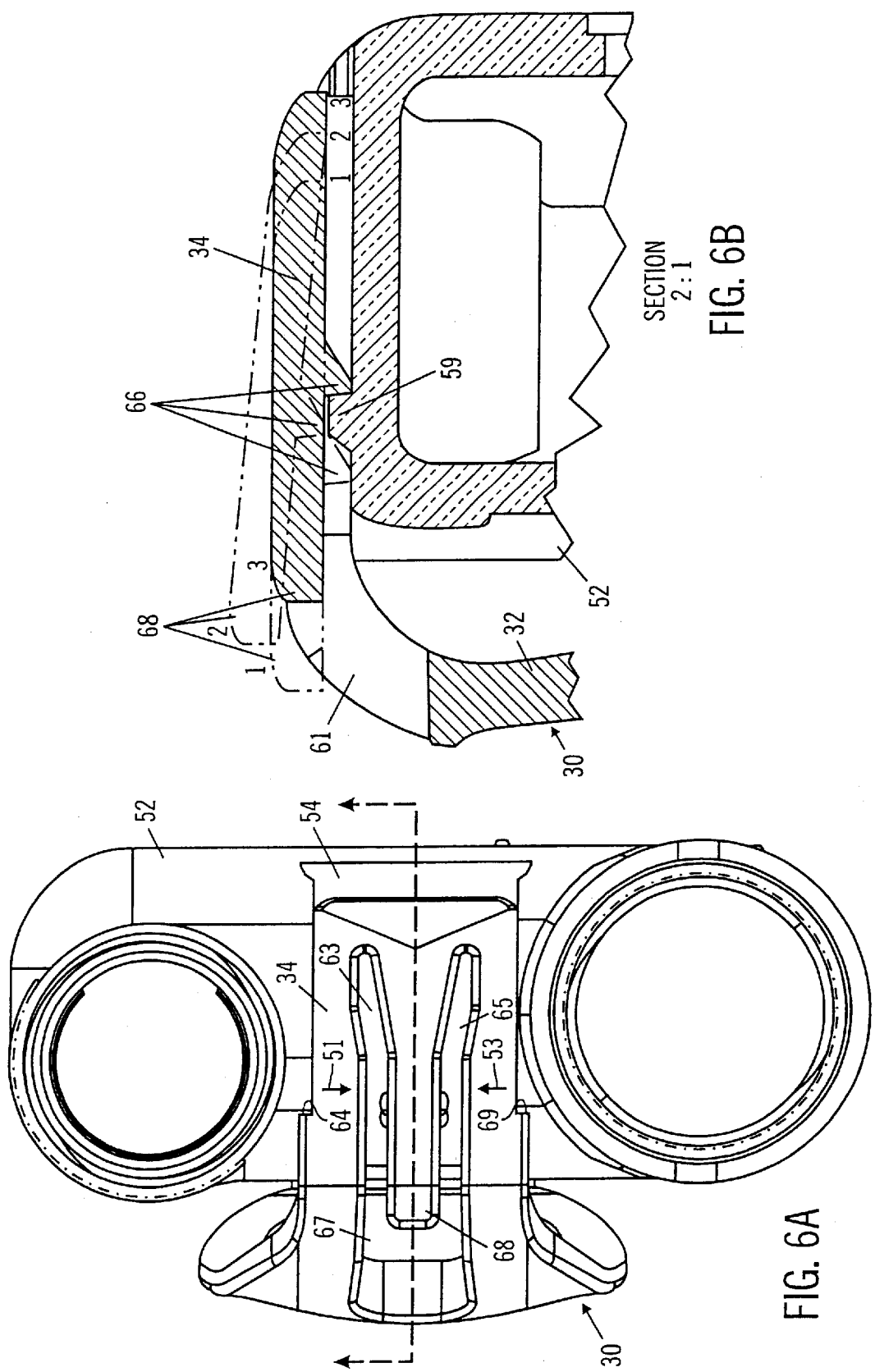

LOW-PROFILE MOUNTING CLIP FOR PERSONAL DEVICE

BACKGROUND OF THE INVENTION

1. Field of the Invention

The present invention relates, generally, to low-profile durable mounting clips for receiving and supporting personal devices (such as personal electronic devices) and, in particular embodiments, to low-profile mounting clips for inconspicuously holding a personal electronic device such as, but not limited to, an infusion device, a medical monitor or other medical device, in a concealed location by attaching the mounting clip to an article of clothing.

2. Description of Related Art

Various personal devices (such as personal electronic devices) are available that are conveniently adapted to be supported by a mounting clip attached to a user's belt or other article of clothing. Examples of such personal devices include mobile phones, pagers, PDAs, as well as medical devices such as medication infusion pumps and medical monitors. The personal devices are typically adapted for mounting onto a patient's waistband, belt, pocket seam or other suitable clothing item, by using a conventional spring-legged belt clip. In this regard, such mounting clips have typically been designed for connection to the housing of the personal devices (such as personal electronic devices), and for clip-on installation onto the patient's clothing.

FIG. 1A illustrates an example of a spring-legged mounting clip connected to an electronic device. FIG. 1A illustrates an example of a personal medical device, which in this example is a Minimed 506 medication infusion pump. FIG. 1A shows a perspective view of medication infusion pump 10 for delivering or dispensing a prescribed medication to a patient. The medication infusion pump 10 includes a housing 12 enclosing the pump and its associated components. A mounting clip 14 is removably secured to one side of medication infusion pump 10, as shown. The mounting clip 14 shown in FIG. 1A is a unitary part molded in the general shape of an over-bent "U" from a material such as polypropylene. The mounting clip 14 incorporates an elastic living hinge to provide the spring force necessary for expanding and retracting the leg of the U-shaped mounting clip 14 for attachment of the electronic device (such as medication infusion pump 10) to an article of clothing.

FIG. 1B illustrates a perspective view of the medication infusion pump 10 shown in FIG. 1A with the mounting clip 14 separated from the housing 12 in order to show a conventional structure for connecting the mounting clip 14 to the housing 12. As shown in FIG. 1B, included on the housing 12 is a dovetail groove 16 designed for slide-fit reception of a matingly shaped corresponding dovetail boss 18 included on the mounting clip 14. The dovetail groove 16 and mating dovetail boss 18 permit manual slide-on attachment and slide-off removal of mounting clip 14.

FIG. 1C shows dovetail boss 18 in more detail. From FIG. 1C it can be seen that dovetail boss 18 has essentially a wedge shape including a base 11 and two sides 13, 15 extending from the base at essentially symmetrical angles to contact the body of one leg of mounting clip 14. The points of contact between sides 13, 15 of the dovetail boss 18 and mounting clip 14 as they extend transversely across one leg of mounting clip 14 define a flex point 17 of width "w." Flex point 17 thus essentially acts like a pivot pin about the axis of which the mounting clip 14 and housing 12 move in relation to each other. Other mounting clip designs may have a groove and mating boss having a generally rectangular shape where the walls of the boss extend upward at essentially 90 degree angles. In that case, the points of contact between the sides of the rectangular boss and the mounting clip may similarly define a flex point that acts like a pivot pin. In either of these configurations, stresses applied to the mounting clip and/or housing are concentrated at the flex point.

Materials used in conventional mounting clip structures are selected to have a suitable elasticity to provide the spring force required for securing the electronic device (such as medication infusion pump 10) to an article of clothing. In addition, selected materials are employed to avoid heat related deformation and stress relaxation. If such materials are not employed, the initial shape of the mounting clip may be compromised. This is illustrated in FIG. 2, where the mounting clip 14, 14' attached to housing 12 is shown with an initial spring force (shown by solid lines) and a compromised spring force (shown in phantom lines) due to stress relaxation that might occur if suitable materials were not used. Once the spring force has been compromised, secure attachment to an article of clothing may be more difficult to achieve.

Some mounting clips employing the dovetail boss/groove configuration are susceptible to inadvertent separation from the personal device. This may occur, for example, when the mounting clip is designed such that only the friction between the dovetail boss and groove maintains the mounting clip on the personal device. A transverse force contacting the personal device in a direction opposite to that of the direction of slide-on mounting of the dovetail boss into the dovetail groove may cause the personal device to inadvertently partially or fully separate from the mounting clip. Furthermore, a force applied in a direction perpendicular to that of the direction of slide-on mounting of the dovetail boss into the dovetail groove and away from the article of clothing may significantly stress the flex point.

Other mounting clip designs have been used which reduce the chances of separation due to a transverse force as described above. For example, a mounting clip for mounting a medication infusion pump to a patient is described in U.S. Pat. No. 5,472,317. The mounting clip comprises a belt clip with a pair of pivotally interconnected and spring-loaded legs adapted for mounting onto a belt or other item of clothing worn by a patient. One leg of the belt clip includes a dovetail key for slide-fit reception into a mating dovetail boss formed in the housing of a medication infusion pump. A detent button is carried on the belt clip at the distal end of a spring arm for snap-fit reception into a detent seat formed in the pump housing, to lock the pump onto the belt clip. The spring arm is manually accessible to permit fingertip retraction of the detent button from the seat, and permit easy sliding removal of the pump housing from the belt clip. Thus, the locking device may provide protection against separation by a transverse force applied to the housing of the medication infusion pump.

SUMMARY OF THE DISCLOSURE

Embodiments of the present invention relate to low-profile, durable mounting clips for holding personal devices (such as, but not limited to, personal medical devices, personal electronic devices, infusion devices, medical monitors, or the like).

In particular embodiments, a mounting clip having an essentially inverted "L" shaped configuration includes a wide foot portion including engagement elements for attachment to corresponding engagement elements on a housing of a personal device. The mounting clip further includes a leg portion for attachment to an undergarment or other suitable article of clothing that acts as a supporting member. A heel portion located between and connecting the leg portion and foot portion allows the leg portion to flexibly and durably retract away from the housing for attachment to the article of clothing. The inverted "L" shaped configuration allows the leg portion to remain closer to the housing, thus providing a lower profile for ease of attachment to undergarments or other concealed locations on the user's person. At the same time, the inverted "L" shaped configuration and the wider foot provides a stronger and more durable connection to the housing. In the context of a medical device such as, but not limited to, an infusion device or medical monitor, embodiments of the mounting clip allow a user of the device to more confidently and comfortably conceal the device by attaching it to an undergarment or other concealed location on the user's person.

A mounting clip according to an embodiment of the invention includes a foot portion having a dovetail configuration with angled facets arranged in a downwardly and outwardly cascading fashion for engaging corresponding surfaces on a dovetail groove provided on the housing of the personal electronic device (for example, an infusion device or medical monitor). The mating angled facets are configured to allow separation with minimal damage, away from the corresponding and opposing dovetail groove on the housing during an overload condition In particular embodiments, the dovetail configuration further includes a tapered portion at the leading edge of the foot for facilitated attachment of the mounting clip to the housing, as well as providing for extra protection against damage to the mounting clip or housing in a overload condition.

Further embodiments of the mounting clip include voids that allow the solid portions of the foot of the mounting clip to flex inwardly, thus facilitating separation of the foot from the housing with minimal damage. Additional embodiments include channels extending along the foot of the mounting clip in the direction of engagement with the housing that provide additional inward flexibility of the foot of the mounting clip.

In other embodiments, a snap tab beam locking mechanism is provided having a barb for interlocking with a bump provided on the housing to lock the engaged mounting clip onto the housing. In yet other embodiments, a rotatable cam locking mechanism is provided having one or more radial snap tabs having engagement elements for engaging corresponding surfaces on the mounting clip. Rotation of rotatable cam locks the mounting clip onto the housing by blocking movement of the mounting clip in a direction opposite to the direction of engagement.

BRIEF DESCRIPTION OF THE DRAWINGS

Referring now to the drawings in which like reference numbers represent corresponding parts throughout:

FIG. 3A shows a perspective view of a mounting clip according to an embodiment of the invention as seen from the back side.

FIG. 3B shows a perspective view of a mounting clip according to an embodiment of the invention as seen from the front side.

FIG. 3C shows a unique dovetail configuration on the foot of a mounting clip according to an embodiment of the invention.

FIG. 5A illustrates a perspective view of a housing for an infusion device for use with embodiments of the invention.

FIG. 5B illustrates a front view of a housing for an infusion device according to embodiments of the invention.

FIG. 5C illustrates a side view of a generally "inverted L" shaped mounting clip according to an embodiment of the invention in contrast to a side view of a conventional "U" shaped mounting clip.

FIG. 5D illustrates a view of a housing for an infusion device according to embodiments of the invention.

FIG. 6A illustrates a top view of a housing with a mounting clip fully engaged with the housing and locked in place according to an embodiment of the invention.

FIG. 6B illustrates a cross sectional side view of a housing and mounting clip, showing progressive steps in the engagement and locking operation of the foot of the mounting clip with a channel in the housing, according to an embodiment of the invention.

DETAILED DESCRIPTION OF PREFERRED EMBODIMENTS

Figures 1A, 1B, 1C:
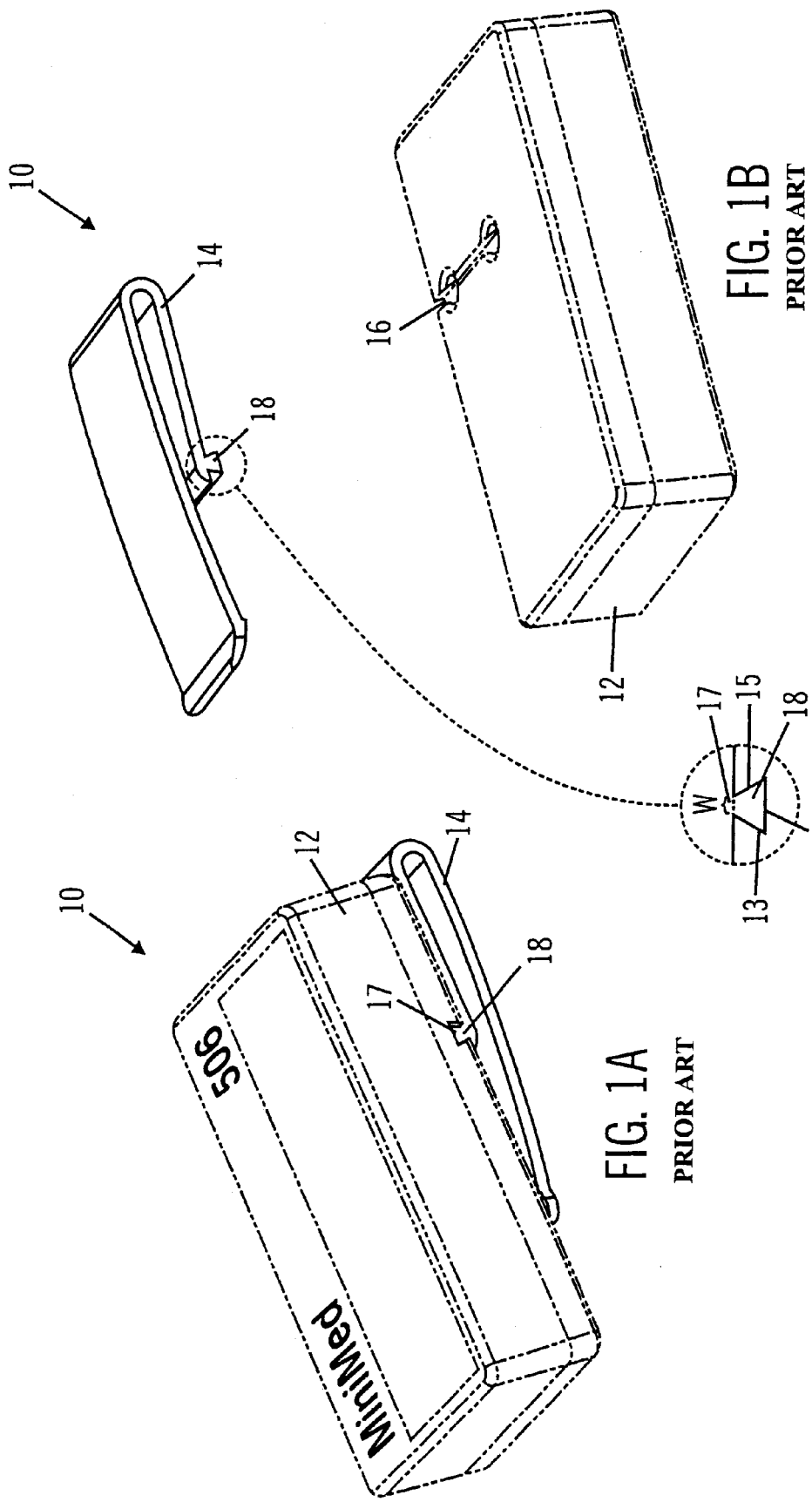
FIG. 1A illustrates an example of a spring-legged mounting clip connected to a medication infusion pump.
FIG. 1B illustrates a perspective view of a medication infusion pump and mounting clip, showing a conventional structure for connecting the mounting clip to the housing of the pump.
FIG. 1C illustrates a dovetail boss.
Figure 2:
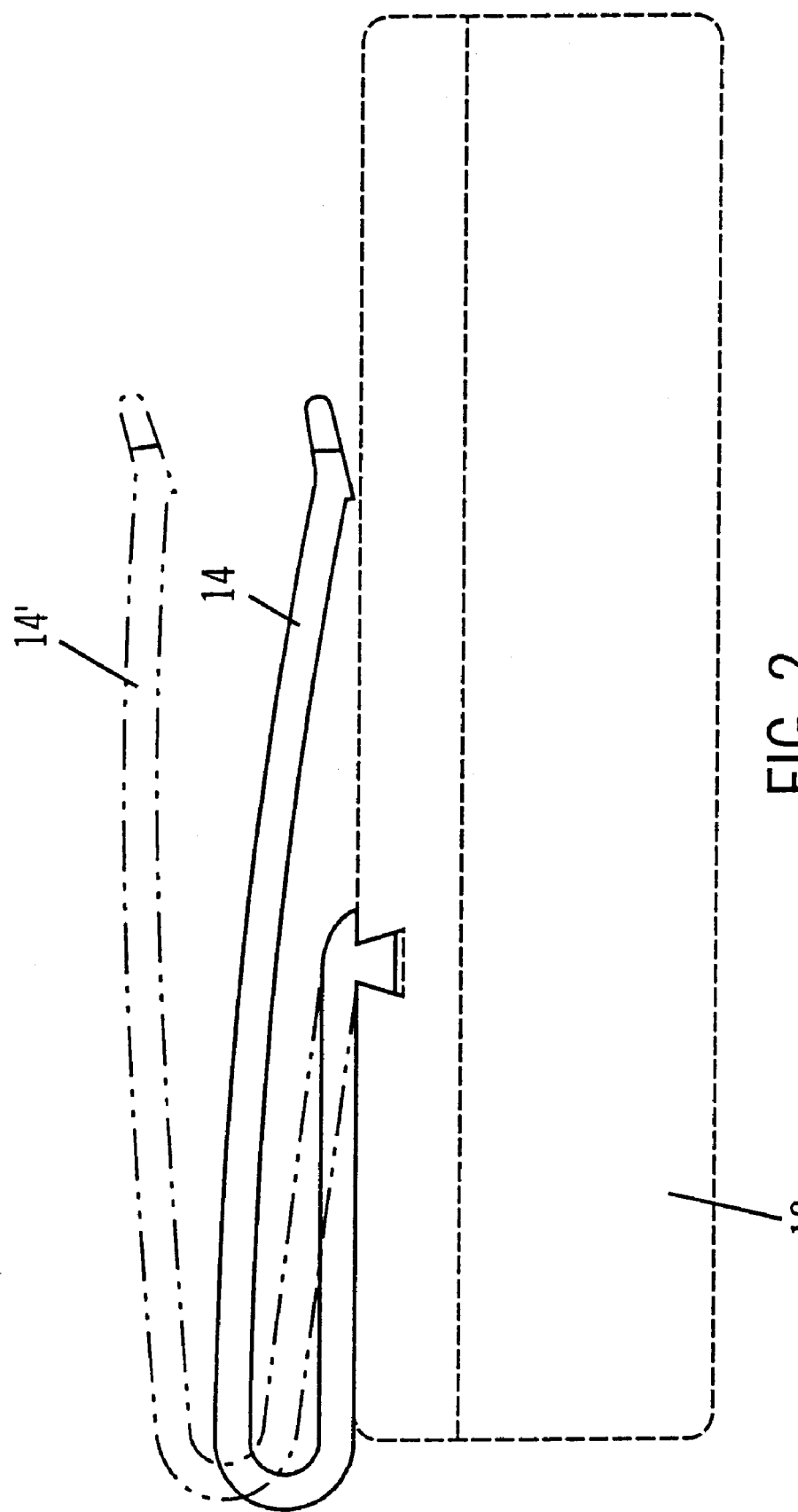
FIG. 2 illustrates a mounting clip attached to a housing and shown with an initial spring force and a compromised spring force.

The following detailed description is of the best presently contemplated mode of implementing the invention. This description is not to be taken in a limiting sense, but is made merely for the purpose of illustrating the general principles of the invention. The scope of the invention is best defined by the appended claims.

As discussed above, embodiments of the present invention relate to low-profile, durable mounting clips for holding personal devices (such as, but not limited to, personal medical devices, personal electronic devices, infusion devices (such as infusion pumps, disposable pumps, constant flow devices, or the like), medical monitors, or the like). In particular embodiments, a mounting clip having an essentially inverted "L" shaped configuration includes a wide foot portion including engagement elements for attachment to corresponding engagement elements on a housing of a personal device. The mounting clip further includes a leg portion for attachment to an undergarment or other suitable article of clothing that acts as a supporting member. A heel portion located between and connecting the leg portion and foot portion allows the foot portion to flexibly and durably retract away from the housing for attachment to the article of clothing. The inverted "L" shaped configuration allows the leg portion to remain closer to the housing, thus providing a lower profile for ease of attachment to undergarments or other concealed locations on the user's person. At the same time, the inverted "L" shaped configuration and the wider foot provides a stronger and more durable connection to the housing. In the context of a medical device such as, but not limited to, an infusion device or medical monitor, embodiments of the mounting clip allow a user of the device to more confidently and comfortably conceal the device by attaching it to an undergarment or other concealed location on the user's person, since the mounting clip has a lower profile than conventional prior art clip designs.

In other embodiments, a snap tab beam locking mechanism is provided having a barb for interlocking with a bump provided on the housing to lock the engaged mounting clip onto the housing. In yet other embodiments, a rotatable cam locking mechanism is provided having one or more radial snap tabs having engagement elements for engaging corresponding surfaces on the mounting clip. Rotation of rotatable cam locks the mounting clip onto the housing by blocking movement of the mounting clip in a direction opposite to the direction of engagement.

A mounting clip according to an embodiment of the present invention is shown in FIGS. 3A and 3B. In FIGS. 3A and 3B, a generally "inverted L" shaped mounting clip 30 (a side view of which is shown in FIG. 5C in contrast to a side view of a "U" shaped mounting clip 14), having a leg portion 32 and a foot portion 34, is shown. FIG. 3A shows a perspective view of mounting clip 30 as seen from the back side, i.e., the side facing away from a housing for a personal device such as, but not limited to, a personal electronic device (not shown) to which mounting clip 30 may be attached. FIG. 3B shows a perspective view of mounting clip 30 as seen from the front side, i.e., the side facing towards a housing for a personal device (not shown) to which mounting clip 30 may be attached.

The foot 34 of mounting clip 30 includes various engagement elements for slideably attaching and securing the mounting clip to a housing of personal device (such as, but not limited to, personal medical devices, personal electronic devices, infusion devices, medical monitors, or the like) having corresponding engagement elements designed to slideably receive and secure the foot 34 of mounting clip 30. The leg 32 of mounting clip 30 is designed such that, when the mounting clip 30 is attached and secured to a housing, at least a first portion of the leg 32 facing the housing, for example portion 36 shown in FIG. 3B, is spaced a distance apart from the housing. Thus, a defined space is provided between the leg 32 and the housing for receiving a strap, belt, or other article of clothing used to support the mounting clip 30. The leg 32 of mounting clip 30 is further designed such that, when attached to a housing, at least a second portion of the leg 32, for example portion 38 shown in FIG. 3B, retractibly abuts a portion of the housing. Thus, the strap, belt, or other article of clothing used to support the mounting clip 30 is enclosed within the defined space defined by the heel 61 and the portion 38.

In one embodiment, mounting clip 30 may be a unitary inverted "L"-shaped part molded from a suitably rigid material such as, but not limited to, polycarbonate. The inverted "L" shape and the more rigid material are employed to provide additional strength to mounting clip 30. The foot 34 of mounting clip 30 may have a length and width (shown as "L" and "W," respectively in FIG. 3A) that provide added strength at a heel 61 (best shown in FIG. 6B) in order to reduce the possibility of compromised spring force due to stress relaxation of the mounting clip 30. Thus, the engaged portion (i.e. foot 34) remains durably secured and substantially stationary relative to the housing. At the same time, the mounting clip 30 has elasticity such that the unengaged portion of mounting clip 30 (i.e., leg 32) is allowed to be retractibly pulled back away from the housing for attachment to an article of clothing. Thus, a spring force is provided for mounting clip 30 while avoiding the drawbacks of clip designs incorporating a living spring, such as stress relaxation of the spring force.

In addition, in one embodiment, mounting clip 30 and the housing are designed such that the foot 34 of the "L" engages a top portion of the housing in a manner that allows the leg 32 to remain closer to the housing, thus reducing the overall thickness of the mounting clip 30/housing combination. Thus, the mounting clip 30/housing combination can have a lower profile and may be more discretely attached by the user to an undergarment or other concealed clothing item than would be possible with conventional prior art clip designs.

The abutting portion 38 of mounting clip 30 may be manually pulled back from the housing for attachment to the article of clothing by, for example, fingertip retraction. Alternatively, the abutting portion 38 may be separated from the housing by sliding a strap, belt, or other article of clothing against the point of contact between the abutting portion 38 and the housing. The strap, belt, or other article of clothing, thus separates and passes between the abutting portion 38 and the housing. When the strap, belt, or other article of clothing clears the abutting portion 38 and enters the defined space, the abutting portion 38 again returns to its abutting position to act as a barrier against inadvertent detachment of the mounting clip 30 from the article of clothing.

In one embodiment, the mounting clip 30 is designed to provide improved protection against inadvertent detachment due to forces exerted transverse to the flex point or heel 61 of mounting clip 30. Further embodiments include additional features on foot 34 of mounting clip 30 that reduce the risk of damage to the mounting clip 30 from an overload condition at the heel 61 due to forces exerted both transverse and perpendicular to mounting clip 30. In addition, in further embodiments, mounting clip 30 may provide a locking feature for locking mounting clip 30 to a housing of a personal device (such as, but not limited to, personal medical devices, personal electronic devices, infusion devices, medical monitors, or the like).

Referring again to FIGS. 3A and 3B, one embodiment of engagement elements for slideably attaching and securing the mounting clip to a housing of a personal device having corresponding engagement elements designed to slideably receive and secure the mounting clip 30 will be described.

In some embodiments, foot 34 includes a multi-faceted dovetail configuration 35 formed along at least a portion of its sides as best shown in FIGS. 3B and 3C. FIGS. 3B and 3C show the faceted dovetail configuration 35 extending for length L' on one side of foot 34. Other embodiments of the multi-faceted dovetail configuration may have other suitable lengths. The other side of foot 34 includes a substantially identical and symmetrical dovetail configuration (not shown). FIG. 3C shows the dovetail configuration 35 of FIG. 3B in more detail. Dovetail configuration 35 may include one or more angled facets (three angled facets 31, 33, 39 are shown in FIG. 3C) arranged in an outwardly and downwardly cascading fashion. In one embodiment, the angled facets are designed such that the uppermost facet in the cascade (facet 31 in FIG. 3C) slopes outwardly and downwardly at a defined angle. The middle facet in the cascade (facet 33 in FIG. 3C) slopes outwardly and downwardly at a defined angle that is steeper than the angle of the uppermost facet. The lowermost facet in the cascade (facet 39 in FIG. 3C) slopes outwardly and downwardly at a defined angle that is steeper than both the angles of both the uppermost and middle facets. The angled facets 31, 33, 39 are designed to slideably engage corresponding engagement elements on a housing. In further embodiments, the dovetail configuration 35 may include a faceted portion 37 on both sides of the leading edge of the dovetail configuration 35 (i.e., the "toe" portion of foot 34) that first engages the corresponding engagement element of the housing. Faceted portions 37 facilitate the initial engagement between the mounting clip 30 and the engagement elements of the housing.

One embodiment of a housing having corresponding engagement elements for receiving the foot 34 of mounting clip 30 is shown in FIGS. 5A and 5B. FIGS. 5A and 5B show perspective and front views, respectively, of a housing 52 for an infusion device. Housing 52 includes on its top surface a channel 54 designed to have a size and shape suitable for receiving the foot 34 of mounting clip 30. In one embodiment, channel 54 is integrally formed with housing 52, for example by a molding process. Other embodiments may form channel 54 by other suitable processes.

FIG. 5D shows a perspective view of housing 52 with its back side to the right, showing channel 54 in more detail. In FIG. 5D, a dovetail groove 56 is shown on one side of channel 54. Channel 54 includes a substantially identical and symmetrical dovetail groove (not shown) on its other side. The dovetail grooves 56 are designed to have a size and shape for slideably receiving the dovetail configurations 35 located on the sides of mounting clip 30 such that the surfaces of the angled facets 31, 33 and 39 are mated to corresponding surfaces (not shown) of the dovetail grooves 56.

In a further embodiment, channel 54 further includes a ramped snap tab bump 59 (best shown in FIG. 5D) which cooperates with a corresponding snap tab barb 66 (best shown in FIG. 6B) located on snap tab beam 68 (best shown in FIG. 6A) to lock mounting clip 30 to housing 52 when fully engaged. The operation of the snap tab beam 68 locking mechanism is described in relation to FIGS. 6A and 6B. FIG. 6A shows a top view of housing 52 with mounting clip 30 fully engaged in channel 54 and locked in place. FIG. 6B shows a cross sectional side view of housing 52 and mounting clip 30 showing progressive steps in the engagement and locking operation of foot 34 with channel 54.

At step 1, as shown in FIG. 6B, the snap tab barb 66 on snap tab beam 68 (shown by phantom lines) approaches snap tab bump 59 as the foot 34 of mounting clip 30 begins to engage channel 54. At step 2, the snap tab barb 66 on snap tab beam 68 (shown by phantom lines) begins to ride over the snap tab bump 59 as the foot 34 of mounting clip 30 further engages channel 54. The snap tab beam 68 is designed such that it elastically flexes in an upward direction to allow the snap tab barb 66 to ride up and over snap tab bump 59. At step 3, the snap tab barb 66 on snap tab beam 68 (shown by solid lines) has overridden the snap tab bump 59 and snapped back to the surface of channel 54. At this point, the foot 34 of mounting clip 30 is fully engaged with channel 54 and locked in place. In one embodiment, channel 54 further includes engagement stops 55 and 57 (FIG. 5D) for abutting against corresponding surfaces 64 and 69 of foot 34 (best shown in FIG. 6A) when full engagement of mounting clip 30 with channel 54 is achieved. The mounting clip 30 may be removed from the housing by lifting up the snap tab beam 68 until the snap tab barb 66 clears the snap tab bump 59 and the mounting clip 30 may be slideably removed in a direction opposite to that of engagement.

As discussed above, in one embodiment, the surfaces of the angled facets 31, 33, and 39 of dovetail configurations 35 are mated to corresponding surfaces of the dovetail grooves 56 when the mounting clip 30 is fully engaged to the housing 52. It is possible that a sufficient force could be exerted on the mounting clip 30 and/or housing 52 to cause an overload condition. An overload condition may result, for example, when a force in a direction other than the direction of engagement between the foot 34 and channel 54 causes the angled facets 31, 33, and 39 to be pushed up against the corresponding surfaces of the dovetail grooves 56 until a separation of the foot 34 from channel 54 occurs, thus causing mounting clip 30 to inadvertently separate from housing 52. In one embodiment, the angled facets 31, 33, and 39 of dovetail configurations 35 are designed in a downwardly and outwardly cascading fashion such that they may elastically deform, slide from facet to facet along the corresponding and opposing surfaces of the housing, and separate from the housing 52 with minimal damage to either the mounting clip 30 or the housing 52. In some embodiments, mounting clip 30 and/or housing 52 may include a material such as, but not limited to, polytetrafluorethylene and aramid fibers, in order to add more lubricity and strength to dovetail configuration 35. The added lubricity allows the angled facets to more easily slide from one facet surface to the next and with reduced resistance to slide along a corresponding and opposing surface of the housing with reduced friction.

In further embodiments, foot 34 of mounting clip 30 may include voids 63, 65, and 67 (best shown in FIG. 6A) formed in the solid material of foot 34 by, for example, a molding process. In the event of an overload condition as described above, voids 63, 65, and 67 allow the solid portions of foot 34 to flex inwardly, as shown by arrows 51 and 53. This inward flexibility allows the engagement elements along the sides of foot 34, for example angled facets 31, 33, and 39 of dovetail configurations 35, to separate with minimal damage away from the corresponding and opposing surface of the housing, for example dovetail grooves 56, during an overload condition. Thus, the engagement elements separate and the mounting clip 30 is free to separate from the housing with minimal damage to either.

In still further embodiments, foot 34 may include channels 77, 79 (best shown in FIG. 3B) that extend along foot 34 in the direction of engagement with housing 52 for a defined length. In one embodiment, channels 77, 79 extend along the bottom of foot 34. Channels 77, 79 provide additional inward flexibility that allows the engagement elements of foot 34 (for example angled facets 31, 33, 39) to separate from corresponding engagement elements (for example angled surfaces of the dovetail grooves 56) with minimal damage under an overload condition. When an overload condition occurs, the engagement elements located along the sides of foot 34 are allowed, due to channels 77, 79 to flex inwardly away from corresponding engagement elements on the housing 52.

In the embodiment of mounting clip 30 shown in FIG. 3A, voids 63, 65, and 67 do not extend completely to the toe of foot 34. Instead a solid portion 76 of foot 34 exists at the toe. Thus, there is reduced inward flexibility at solid portion 76. In this embodiment, tapered portions 89 (FIG. 3B) may reduce binding within the dovetail connection and facilitate disengagement of solid portion 76 from the corresponding and opposing surface of the housing by providing a taper along both sides of the foot 34 at the solid portion 76 of the toe.

In various embodiments described above, an integrally formed snap tab beam/barb configuration is employed for locking the fully engaged mounting clip to the housing. Such a configuration has advantages. For example, it requires less material in the foot portion due to the voids therein and may provide improved flexibility to the leg portion of the mounting clip.

Figure 4B:
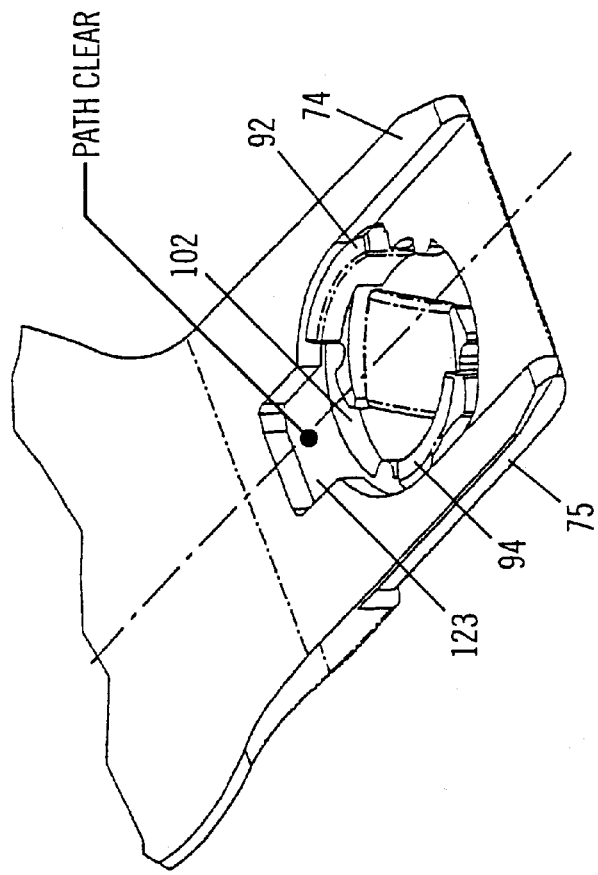
FIG. 4B illustrates a rotatable cam fully attached to a housing and in an unlocked position, according to an embodiment of the invention.
Figure 4A:
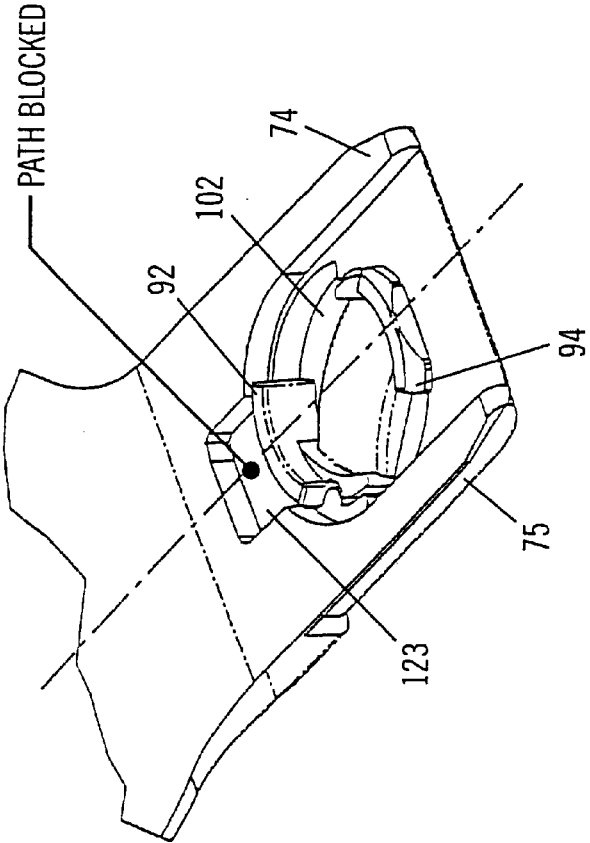
FIG. 4A illustrates a rotatable cam fully attached to a housing and in a locked position, according to an embodiment of the invention.
Figure 7C:
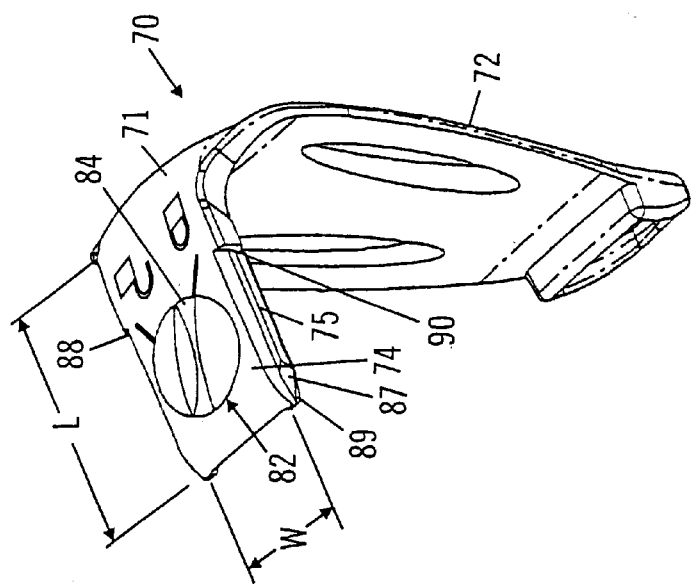
FIG. 7C illustrates a perspective view of a mounting clip having a rotatable cam locking mechanism, according to an embodiment of the invention.
Figure 7B:
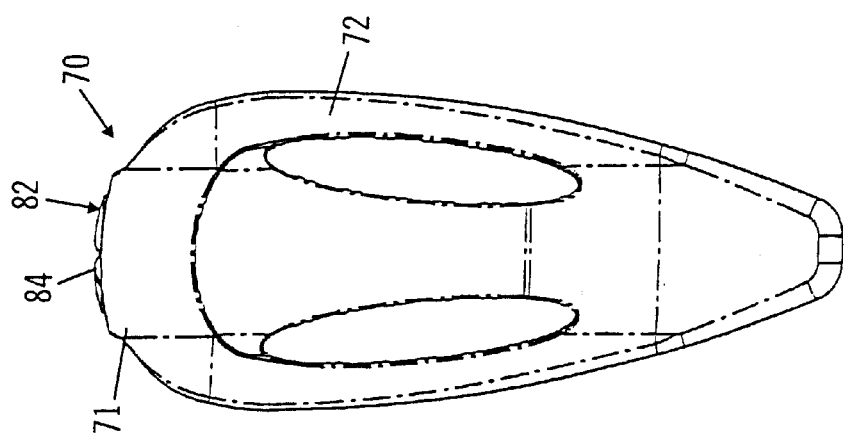
FIG. 7B illustrates a back view of a mounting clip having a rotatable cam locking mechanism, according to an embodiment of the invention.
Figure 7A:
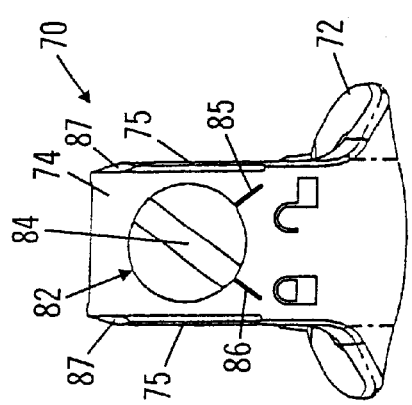
FIG. 7A illustrates a top view of a mounting clip having a rotatable cam locking mechanism, according to an embodiment of the invention.

A mounting clip having another type of locking mechanism is shown in the embodiment of FIGS. 7A, 7B and 7C. FIGS. 7A, 7B and 7C show top, back and perspective views, respectively, of mounting clip 70. Embodiments of mounting clip 70 replace the snap tab beam/barb locking configuration with a rotatable cam 82 locking feature for locking the mounting clip 70 to a housing 52. As described and illustrated above, the snap tab beam/barb configuration provided a barb 66 located on a snap tab beam 68 for riding up and over a bump 59 located on housing 52 for locking the mounting clip to the housing 52. In contrast, embodiments of the rotatable cam 82 locking feature include one or more radial snap tabs 92, 94 positioned on the rotatable cam 82. The one or more radial snap tabs 92, 94 are positioned such that when rotatable cam 82 is in the unlocked position 85, a clear path is provided for slideably attaching the mounting clip 70 to housing 52 (best shown in FIG. 4B). When rotatable cam 82 is fully attached to housing 52 and is rotated to the locked position 86, at least one of the radial snap tabs 92, 94 is positioned such that it aligns, in an essentially parallel manner, with the flat surface of a bump located on the housing. Thus, the mounting clip 70 is blocked by the bump from moving in a direction opposite to that of the direction of attachment (best shown in FIG. 4A). Therefore, a more convenient method of locking the mounting clip 70 to the housing is provided. The rotatable cam 82 locking feature is also advantageous in that it adds more durability to the mounting clip 70 because more material is used in the foot 74, increasing its rigidity.

The rotatable cam 82 may, in one embodiment, be formed, for example by molding, separately from the remainder of the mounting clip. The rotatable cam 82 may subsequently be inserted into an opening 102 formed, for example by molding, in the foot 74 of the mounting clip 70 and designed to have a size and shape for receiving the rotatable cam 82. The opening 102 may include, along its sides, one or more engagement stops for abutting against corresponding surfaces formed on the inserted rotatable cam 82. In one embodiment, the engagement stops are opposing, symmetrical mechanical stops 105, 107 that limit the rotation of the rotatable cam 82 to 75 degrees between unlocked and locked positions. Other embodiments may employ other engagement stop configurations.

In further embodiments, the rotatable cam 82 may include a notch 84 for insertion of a coin, key, paper clip, credit card or other suitable tool that may be used to rotate the rotatable cam 82 between locked and unlocked positions. In still other embodiments, the rotatable cam 82 may include dual opposing snap tab features that provide audible and tactile indicators to indicate to a user that the rotatable cam 82 is in a locked position. In one embodiment, visual indicators of the same may be included on the mounting clip and/or housing as well.

In another embodiment, one or more of the dimensions of the rotatable cam 82 and opening 102 are selected to result in a frictional fit between the rotatable cam 82 and the opening. The frictional fit is sufficient to maintain the rotatable cam 82 firmly in intermediate positions between the unlocked and locked positions.

FIGS. 7A, 7B and 7C show top, back and perspective views, respectively, of mounting clip 70, having a leg portion 72, a foot portion 74 and a heel portion 71. In one embodiment, mounting clip 70 may have a generally inverted "L"-shape and may include two or more parts molded from a suitably rigid material such as, but not limited to, a polycarbonate. As in the previous embodiment discussed above, the inverted "L" shape and the more rigid material are employed to provide additional strength to mounting clip 70. The foot 74 of mounting clip 70 may have a length and width (shown as "L" and "W," respectively in FIG. 7C) that provide added strength at a heel 71 in order to reduce the possibility of compromised spring force due to stress relaxation of the mounting clip 70. Furthermore, as discussed above, added durability may be provided by the increased material used in foot 74 of mounting clip 70 as opposed to foot 34 of mounting clip 30. Thus, the engaged portion (i.e. foot 74) remains durably secured and substantially stationary relative to the housing 52 (shown in FIGS. 5A, 5B and 5D). At the same time, the mounting clip 70 has elasticity such that the unengaged portion of mounting clip 70 (i.e., leg 72) is allowed to be retractibly pulled back away from the housing for attachment to an article of clothing. Thus, a spring force is provided for mounting clip 70 while avoiding the drawbacks of clip designs incorporating a living spring, such as stress relaxation of the spring force.

As can be seen from FIGS. 7A and 7C, embodiments of mounting clip 70 may additionally include a dovetail configuration 75 along the sides of foot 74 having one or more angled facets that are designed to slideably engage corresponding engagement elements on housing 52. In further embodiments, the dovetail configuration 75 may include faceted portions 87 on both sides of the toe of the dovetail configuration 75. The details and advantages of the dovetail configuration 75 and faceted portions 87 have been discussed above in relation to mounting clip 30. Further embodiments may include engagement stops 88 and 90 for abutting against corresponding surfaces 55 and 57 (FIG. 5D) of housing 52 when full engagement of mounting clip 70 with channel 54 is achieved. In still further embodiments, mounting clip 70 and/or housing 52 may include a material such as, but not limited to, polytetrafluorethylene and aramid fibers, to add more lubricity and strength to dovetail configuration 75. The added lubricity has the advantages discussed above in relation to mounting clip 30.

Figure 8A:
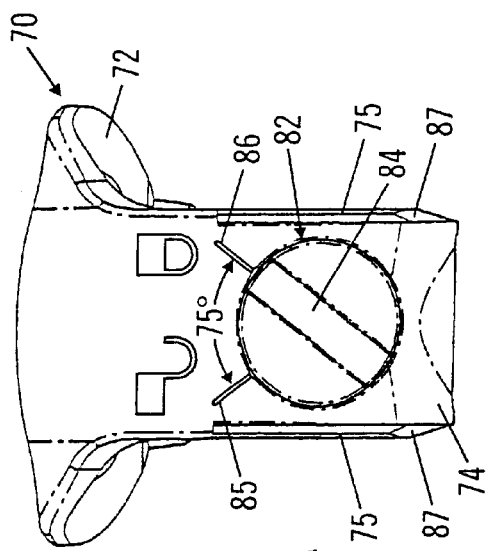
FIG. 8A illustrates a top view of a rotatable cam locking mechanism in a locked position, according to an embodiment of the invention.
Figure 8B:
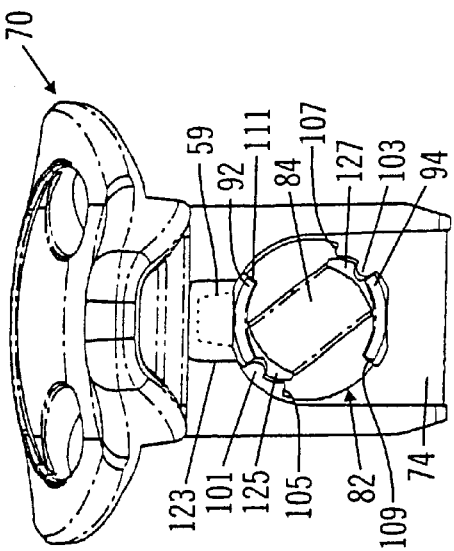
FIG. 8B illustrates a bottom view of a rotatable cam locking mechanism in a locked position, according to an embodiment of the invention.
Figure 8C:
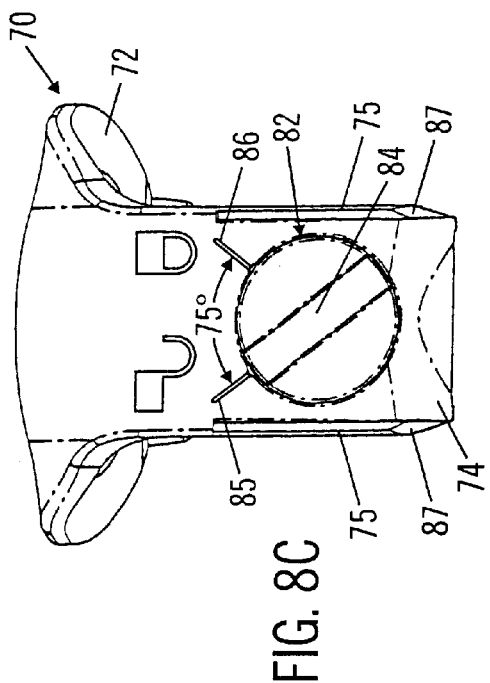
FIG. 8C illustrates a top view of a rotatable cam locking mechanism in an unlocked position, according to an embodiment of the invention.
Figure 8D:
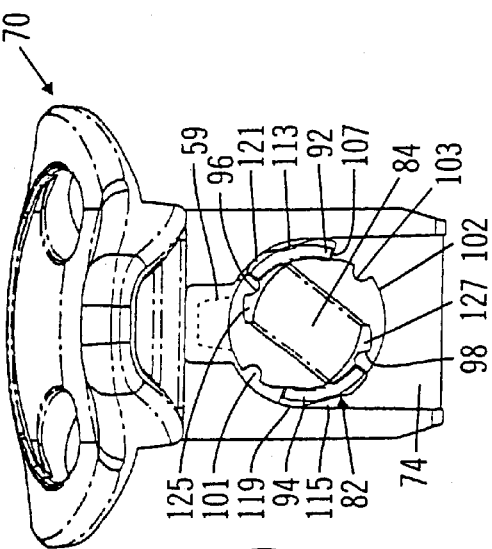
FIG. 8D illustrates a bottom view of a rotatable cam locking mechanism in an unlocked position, according to an embodiment of the invention.

FIGS. 8A and 8B show top and bottom views, respectively, of rotatable cam 82 in the locked position. FIGS. 8C and 8D show top and bottom views, respectively, of rotatable cam 82 in the unlocked position. As discussed above, in one embodiment, rotatable cam 82 may be rotated, for example by a coin inserted in notch 84, between an unlocked position 85 and a locked position 86. In on embodiment, the rotational span between unlocked position 85 and a locked position 86 may be approximately 75 degrees (as shown in FIGS. 8A and 8B). Other embodiments may employ different rotational spans.

In one embodiment, rotatable cam 82 includes two essentially symmetrical radial snap tabs 92, 94 positioned on opposing sides of the rotatable cam 82. The radial snap tabs 92, 94 include integrally formed and essentially symmetrical indentations 96, 98 designed for snap-fit reception of matingly shaped corresponding buttons 101, 103 integrally formed on the sides of opening 102. Further embodiments include engagement stops 105, 107 (best shown in FIG. 8B) for abutting against corresponding surfaces 109, 111 on radial snap tabs 92, 94 when rotatable cam 82 is in the unlocked position 85 (as shown in FIG. 8D).

In one embodiment, radial snap tabs 92, 94 further include on their outer walls flat surfaces 113, 115 (best shown in FIG. 8D) designed to abut a corresponding flat surface 117 on bump 59 (FIG. 5D). Indentation 123 is integrally formed in foot 74 to provide clearance for bump 59 when the mounting clip 70 is fully engaged with housing 52. Thus, when the mounting clip 70 is fully engaged with housing 52 and rotatable cam 82 is in the locked position 86, bump 59 (as shown by phantom lines) will be positioned within indentation 123 with its flat surface 117 abutting flat surface 113 on radial snap tab 92.

Although, according to one embodiment, for a particular orientation of rotatable cam 82, only one of radial snap tabs 92, 94 can contact bump 59 when in the locked position (radial snap tab 92 as shown in FIGS. 8B and 8D), rotatable cam 82 is designed to be symmetrical such that, when inserted in opening 102 during the manufacturing process, it does not require a specific orientation. Thus, however the rotatable cam 82 is oriented when inserted in opening 102 during manufacturing, a flat side of radial snap tabs 92, 94 will abut flat surface 117 on bump 59 when in the locked position 86.

Further embodiments of radial snap tabs 92, 94 may include barbs 119, 121 or similar structures integrally formed with the radial snap tabs 92, 94 that facilitate retention of rotatable cam 82 within opening 102 by overhanging the outside diameter of opening 102 and thus reduce the chances of separation of rotatable cam 82 from mounting clip 70.

In one embodiment, the locking mechanism of the rotatable cam 82 operates in the following manner. As rotatable cam 82 is rotated from the unlocked position 85 towards the locked position 86, a leading edge of radial snap tab 92 encounters the flat surface 117 of bump 59. As rotatable cam 82 continues to rotate towards the locked position 86, radial snap tab 92 begins to elastically bend or compress back as it continues to encounter bump 59. Within a short rotational span after the leading edge of radial snap tab 92 encounters the flat surface 117 of bump 59, the leading edges 125, 127 of indentations 96, 98 begin to contact matingly shaped corresponding buttons 101, 103 and similarly begin to bend or compress back, thus facilitating the angular displacement of radial snap tab 92 as a whole.

As rotatable cam 82 continues to rotate towards the locked position 86, an over center, cam action is created by the compressed material. The over center, cam action facilitates the completion of the rotation and flat surface 113 of radial snap tab 92 aligns, in an essentially parallel manner, with the flat surface 117 of bump 59. Also, substantially simultaneously, as the flat surface of radial snap tab 92 aligns with the flat surface 117 of bump 59, indentations 96, 98 align with matingly shaped corresponding buttons 101, 103. Thus, the radial snap tab 92 and indentations 96, 98 snap fit to the flat surface 117 of bump 59 and matingly shaped corresponding buttons 101, 103, respectively. Thus, the locked position 86 is achieved.

Further embodiments of mounting clip 70 are designed to provide the user with audible, visible and/or tactile indicators to indicate that rotatable cam 82 is in the locked position 86. In some embodiments, the engagement elements of the rotatable cam 82, for example indentations 96, 98 of radial snap tab 92, are designed to produce a sound such as, but not limited to, an audible click or snap when achieving a snap fit with the corresponding engagement elements located on foot 74, for example buttons 101, 103. In other embodiments, the engagement elements of the rotatable cam 82 are designed to produce, in the alternative or in addition to the audible click or snap, a tactile feel indicating a locked position 86. Yet other embodiments are designed to produce tactile and/or audible indicators indicating that the rotatable cam 82 is disengaging from the locked position 86. Still other embodiments may include visual indicators of the unlocked position 85 and locked position 86, such as, but not limited to, silk screened text, pictures, or other indicia indicating the unlocked and locked positions.

In one embodiment, to facilitate manufacturing of mounting clip 70, the design of the rotatable cam 82 incorporates a chamfer, taper or similar edge configuration along the bottom edges of rotatable cam 82 and/or along the top edges of opening 102 to assist in the snap fit assembly of the rotatable cam 82 to the foot 74 of mounting clip 70. Thus, the rotatable cam 82 may, for example, be seated and press fit into opening 102. As the rotatable cam 82 is press fit into opening 102, the radial snap tabs 92, 94 elastically bend or compress inward and allow rotatable cam 82 to seat in opening 102, whereupon the radial snap tabs 92, 94 return to their original position. In another embodiment, one or more of the dimensions of the rotatable cam 82 and opening are selected to result in a frictional fit between the rotatable cam 82 and the opening sufficient to maintain the rotatable cam 82 firmly in intermediate positions between the unlocked and locked positions. In further embodiments, barbs 119, 121 facilitate retention of rotatable cam 82 within opening 102, once seated, by overhanging the outside diameter of opening 102, thus reducing the chances of separation of rotatable cam 82 from mounting clip 70 due to flexing of foot 74. As discussed above, in one embodiment, rotatable cam 82 is designed to be symmetrical such that, when inserted in opening 102 during the manufacturing process, it does not require a specific orientation.

In preferred embodiments, the mounting clips described above are manufactured in an economical manner. According to one embodiment, the mounting clip is integrally formed as a one piece structure. In other embodiments, the mounting clip is assembled from two or more pieces that are formed separately. Such components may be formed from any suitable materials such as plastics, polymers, or the like, having suitable strength, durability and resiliency. Such components may be formed by molding, stamping, machining, combinations or processes, or other suitable manufacturing processes.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A mounting clip for removably attaching a personal device to a supporting member, comprising:
   a foot portion having first engagement elements formed for slide-on attachment and slide-off removal of the personal device;
   a leg portion for mounting the mounting clip on the supporting member;
   a heel portion located between and connecting the foot portion and the leg portion, the heel portion providing a spring force; and
   a rotatable cam locking mechanism having a cam disposed on and rotatable relative to the foot portion, the cam including one or more radial snap tabs having second engagement elements for engaging corresponding surfaces on the foot portion of the mounting clip.

2. The mounting clip recited in claim 1, wherein the first engagement elements include a cascading facet configuration.

3. The mounting clip recited in claim 1, wherein the second engagement elements include indentations and the corresponding surfaces on the mounting clip include corresponding matingly shaped buttons for snap fit connection to the indentations.

4. The mounting clip recited in claim 3, wherein the one or more radial snap tabs include flat surfaces designed to abut a corresponding flat surface on a bump on the personal device when the mounting clip is fully engaged with the personal device and rotated to a locked position.

5. A personal device for attachment to a supporting member, comprising:
   a housing having a channel on a surface, the channel including first engagement elements for receiving a mounting clip, the mounting clip including:
      a foot portion having second engagement elements formed for engaging the first engagement elements for slide-on attachment and slide-off removal of the housing;
      a leg portion for mounting the mounting clip on the supporting member;
      a heel portion located between and connecting the foot portion and the leg portion, the heel portion providing a spring force; and
      a rotatable cam locking mechanism for locking and unlocking the mounting clip to the housing, the rotatable cam locking mechanism having a cam disposed on and rotatable relative to the foot portion.

6. The personal device recited in claim 5, wherein the rotatable cam locking mechanism includes one or more radial snap tabs having third engagement elements for engaging corresponding surfaces on the foot portion.

7. The mounting clip recited in claim 5, wherein the second engagement elements include a cascading facet configuration.

8. A personal device for attachment to a supporting member, comprising:
   a housing having a channel on a surface, the channel including first engagement elements for receiving a mounting clip, the mounting clip including:
      a foot portion having second engagement elements formed for engaging the first engagement elements for slide-on attachment and slide-off removal of the housing;
      a leg portion for mounting the mounting clip on the supporting member;
      a heel portion located between and connecting the foot portion and the leg portion, the heel portion providing a spring force; and
      a rotatable cam locking mechanism for locking and unlocking the mounting clip to the housing, the rotatable cam locking mechanism including one or more radial snap tabs having third engagement elements for engaging corresponding surfaces on the foot portion;
   wherein the channel includes a bump for cooperating with at least one of the radial snap tabs to lock the mounting clip to the housing.

9. The mounting clip recited in claim 8, wherein the radial snap tabs include flat surfaces designed to abut a corresponding flat surface on the bump when the mounting clip is fully engaged with the personal device and rotated to a locked position.

10. The mounting clip recited in claim 8, wherein the third engagement elements include indentations and the corresponding surfaces on the mounting clip include corresponding matingly shaped buttons for snap fit connection to the indentations.

11. The mounting clip recited in the rotatable cam locking mechanism has a locked position and an unlocked position.

12. The mounting clip recited in claim 11, wherein the rotatable cam locking mechanism is rotatable between the locked position and the unlocked position.

13. The mounting clip recited in claim 12, wherein a rotational span between the locked position and the unlocked position is equal to approximately 75 degrees.

14. The mounting clip recited in claim 11, wherein the rotatable cam locking mechanism, when rotated towards the locked position, causes a leading edge of at least one radial snap tab to encounter a flat surface of the bump and elastically bend back such that an over center, cam action facilitates the completion of the rotation and a flat surface of the at least one radial snap tab aligns, in an essentially parallel manner, with the flat surface of the bump.

15. The mounting clip recited in claim 14, wherein the alignment of the bump with the at least one radial snap tab locks the mounting clip to the housing.

16. The mounting clip recited in claim 14, wherein the rotatable cam locking mechanism, when rotated towards the locked position, further causes leading edges of the indentations to encounter the buttons and elastically bend back such that, when aligned, the indentations and the buttons form a snap fit connection.

17. The mounting clip recited in claim 16 wherein the alignment of the flat surface of the at least one radial snap tab and the flat surface of the bump occurs substantially simultaneously with the alignment of the indentations with the buttons.

18. The mounting clip recited in claim 16, wherein the snap-fit connection produces at least one of an audible indicator and a tactile indicator.

19. A mounting clip for removably attaching a personal device to a supporting member, wherein the personal device includes a channel and a protrusion, the mounting clip comprising:
   a foot portion configured to slide into and slide out of the channel on a personal device;
   a leg portion for supporting the foot portion on the supporting member; and
   a rotatable cam locking mechanism having a cam disposed on and rotatable relative to the foot portion between a first rotated position and a second rotated position, the cam including at least one tab for engaging the protrusion on the personal device and inhibiting the foot portion from sliding out of the channel on the personal device upon the foot portion being in the channel on the personal device and the cam being in the first rotated position, and for avoiding engagement with the protrusion on the personal device and allowing the foot portion to slide into or out of the channel on the personal device when the cam is in the second rotated position.

20. A mounting clip as recited in claim 19, further comprising a heel portion located between and connecting the foot portion and the leg portion, the heel portion providing a spring force.

21. A mounting clip as recited in claim 19, wherein the foot portion includes at least one stop member for engaging the at least one tab of the rotatable cam and stopping rotation of the cam at the first rotated position.

22. A mounting clip as recited in claim 21, wherein the at least one stop member comprises at least one of an audible, tactile and visual indicator, to indicate when the cam is in the first rotated position.

23. A mounting clip as recited in claim 19, wherein the foot portion includes at least one stop member for engaging the at least one tab of the rotatable cam and stopping rotation of the cam at the first rotated position and at the second rotated position.

24. A mounting clip as recited in claim 23, wherein the at least one stop member comprises at least one of an audible, tactile and visual indicator, to indicate when the cam is in the first rotated position and when the cam is in the second rotated position.

* * * * *